United States Patent [19]

Ito et al.

[11] Patent Number: 4,536,398
[45] Date of Patent: Aug. 20, 1985

[54] ANTIVIRAL AGENTS

[75] Inventors: Tatsuo Ito, Isehara; Kazunori Oba, Yokohama; Harumi Fukuyasu, Yokosuka; Tomizo Niwa; Takashi Shomura, both of Yokohama; Yuzo Kazuno, Hachioji, all of Japan

[73] Assignee: Meiji Seika Kaisha Ltd., Tokyo, Japan

[21] Appl. No.: 624,786

[22] Filed: Jun. 25, 1984

Related U.S. Application Data

[63] Continuation-in-part of Ser. No. 544,448, Oct. 21, 1983, abandoned.

[30] Foreign Application Priority Data

Oct. 28, 1982 [JP] Japan ............................... 57-188116

[51] Int. Cl.³ ...................... A01N 31/00; A61K 31/70
[52] U.S. Cl. ......................................... 514/43; 536/23; 536/24

[58] Field of Search .................. 424/180, 181; 536/23, 536/24

[56] References Cited

PUBLICATIONS

Meiji Seika Kaisha, Antibiotic SF–2140, Chemical Abstracts 97: 214253m, (1982).

Primary Examiner—Nicky Chan
Assistant Examiner—Charles H. Thieman
Attorney, Agent, or Firm—Frishauf, Holtz, Goodman & Woodward

[57] ABSTRACT

Disclosed is an antiviral agent comprising as an active component a substance SF-2140 described in detail in the specification, and a pharmaceutically acceptable carrier. Also disclosed is a method for treatment of viral diseases comprising administering a pharmaceutically effective amount of the substance SF-2140.

2 Claims, 3 Drawing Figures

ANTIVIRAL AGENTS

This application is a continuation-in-part of application Ser. No. 544,448, filed Oct. 21, 1983, now abandoned.

This invention relates to a novel antiviral agent. More particularly, it is concerned with a novel antiviral composition which comprises as an active ingredient an antibiotic substance SF-2140.

This invention is described below in detail with reference to the accompanying drawings.

Figure 1:
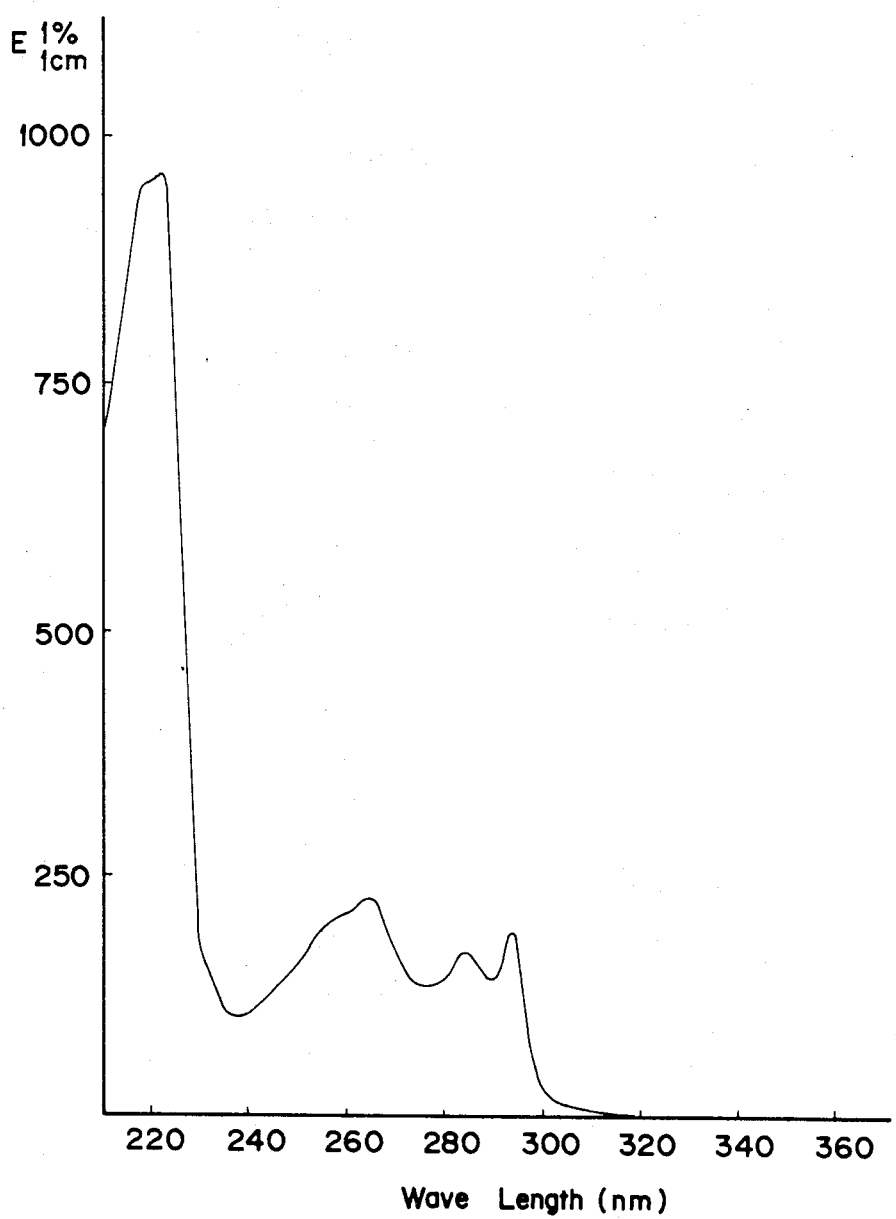
FIG. 1 shows an ultra violet absorption spectrum of the substance SF-2140 in methanol.

It has been previously found that an antibiotic substance named Sf-2140 can be produced by cultivation of actinomycetes belonging to the genus Actinomadura in a nutrient medium as a result of studies on new and useful antibiotic substances having an antibacterial activity against gram-positive and -negative bacteria, and also established physicochemicaland biological properties of the so-isolated substance SF-2140, as disclosed in Japanese Unexamined Patent Publication No. 85397/1982.

As one example of the substance SF-2140-producing microorganisms belonging to the genus Actinomadura, there is mentioned the strain SF-2140 isolated from a soil sample collected in Hyogo-prefecture, Japan in September, 1979.

This SF-2140 strain has the following morphological and physiological properties:

I. Morphological properties

Substrate mycelium extends well-branched and not disrupted under ordinary conditions. Aerial mycelium generally grows abundantly and arthrospore is well formed. Aerial mycelium forms simple branches which are not elustered; no sporangium and sclerotium observed; a straight chain of spores observed all over the aerial mycelium; and no flagella spores observed. Electron microscopic examination shows spores are oval to cylindrical in shape and 0.4 to 0.6×0.6 to 1.3μ in size, long spore chains of scores or more are observed and spore surface is smooth.

II. Growth on various culture media

| Culture medium | Growth and color on reverse | Aerial mycelium | Soluble-pigment |
|---|---|---|---|
| Sucrose-nitrate agar | Good, rusty greenish blue (5 le) | Abundant, white (a) | None |
| Glucose-asparagine agar | Moderate, topaz (3 ne) | Abundant, pearl (3 ca) | None |
| Glycerol-asparagine agar | Good, red greenish blue (4 ne) | Abundant, white (a) | None |
| Starch agar | Good, dark red greenish blue (4 pg) | Abundant, white (a) | None |
| Oatmeal agar | Good, semi-greenish blue (2 ge) | Abundant, white (a) | None |
| Yeast extract-malt extract agar | Good, rusty brown (5 pg) | Abundant, white (a) | None |
| Tyrosine agar | Good, deep brown (4 pl) | Abundant, pearl (3 ba) | None |
| Nutrient agar | Good, cocoa brown (2 fb) | Poor, white (a) | None |

The above results were obtained after cultivation at 28° C. over 14 to 21 days. Color standards indicated in parentheses in the above Table were determined according to the color classification as taught in "Color Harmony Manual", Container's Corporation of America.

III. Physiological properties (1) Temperature range for growth (on starch agar): 20° to 45° C., good growth at 25° to 45° C.

(2) Liquefaction of gelatin: Positive (3) Hydrolysis of starch: Positive (4) Peptonization of skim milk: Negative (5) Coagulation of skim milk: Positive (6) Melanin formation: Negative (7) Nitrate reduction: Negative (8) Salt resistance: Growth at 5% or lower of NaCl, no growth at 7% or higher.

IV. Utilization of carbon source

Basal medium (0.5% yeast extract, 0.1% calcium carbonate and 1.5% agar) containing 1% each of the following carbon sources.

| | |
|---|---|
| D-glucose | + |
| D-fructose | + |
| D-xylose | + |
| L-arabinose | + |
| D-mannitol | + |
| L-rhamnose | + |
| sucrose | + |
| I-inositol | − |
| raffinose | − |

+: utilized
−: not utilized

V. Whole cell analysis

Methods taught by Becker et al (Appl. Microbiol., 12, 421–423, 1964) and by M. P. Lechevalier et al (International Journal of Systematic Bacteriology, 20, 435–443, 1970) were used for analysis.

(1) 2,6-Diaminopimolic acid in whole cells: meso type (2) Saccharides in whole cells: No arabinose and xylose contained with a minor amount of madurose.

From the foregoing properties, the SF-2140 strain may morphologically resemble the genus Streptomyces, but the strain is to be clearly distinguished from the genus Streptomyces, in view of meso-2,6-diaminopimelic acid contained in whole cells, and also from the typical Nocardia genus, in view of no arabinose contained in whole cells. Based upon the system as taught by M. P. Lechevalier et al., supra, the strain SF-2140 can be most reasonably regarded as belonging to the genus Actinomadura. Therefore, the strain SF-2140 has been named as Actinomadura sp. SF-2140. The strain SF-2140 has been deposited under international deposit with accession number FERM BP-386, dated September 9, 1980, in Fermentation Research Institute, Agency of Industrial Science & Technology, Ministry of International Trade & Industry, Japan.

As seen in other actinomycetes, the strain SF-2140 is susceptible to variation in nature and may be easily variable artificially, for example, by using ultraviolet ray, X-ray, high frequency current, radiation, medicines and the like. Any variants and mutants of the strain SF-2140 may be usable for this invention if they have a productivity of the substance SF-2140. Moreover, any substance SF-2140-producing strains belonging to the genus Actinomadura may be employed for this invention.

For production of the antibiotic substance SF-2140, a SF-2140 substance-producing microorganism belonging to the genus Actinomadura is cultivated on a culture medium and the substance SF-2140 is recovered from a cultured broth. More specifically, the said microorganism is cultivated in a culture medium containing those nutrients utilizable by ordinary microbes. As nutrient sources, there may be employed any well-known nutrients commonly used for cultivation of actinomycetes. For instance, there may be employed as a carbon source, such as glucose, sucrose, starch, glycerol, corn syrup, molasses, soybean oil and the like. As a nitrogen source, there may be mentioned, for example, soybean meal, wheat embryo, meat extract, peptone, yeast extract, corn steep liquor, ammonium sulfate, sodium nitrate and the like. If necessary, there may be further incorporated an inorganic salt such as calcium carbonate, sodium chloride, potassium chloride, phosphates and so on and any organic or inorganic substance capable of promoting growth of the strain and production of the substance SF-2140. Cultivation may generally be conducted according to conventional cultivation procedures for production of antibiotic substances and, particularly, submerged culture in a liquid medium is most preferable. Cultivation may be conducted under aerobic condition, cultivation temperature is usually 25° to 37° C., but favourably around 28° C. Maximum production of the substance SF-2140 can be achieved in 2 to 6 days at both shaken culture and tank culture.

For assay of the substance SF-2140, bioassay agar is used as a medium for assay and *Vibrio percolance* is as a test microbe. In this assay, the substance SF-2140 shows a linear relationship between logarithm of concentration and diameter of inhibition zone at 1000 mcg/ml to 125 mcg/ml and the diameter of inhibition zone is 22.0 to 14.6 mm, respectively, according to a paper disc plate method.

For recovery of the substance SF-2140 from a cultured broth, there may be applied for its extraction and purification a synthetic adsorbent such as Amberlite XAD-2 (available from Rohm & Haas Co., U.S.A.), Diaion HP-20 (available from Mitsubishi Chemical Industries Ltd., Japan); a gel filtering agent such as Sephadex LH-20 (available from Pharmacia Fine Chemicals, Sweden); precipitation with hexane; extraction with a solvent, e.g. ethyl acetate: column chromatography with silica gel; and the like. More efficiently, mycelia and other solid materials may be filtered off from a cultured broth by using a filter aid, e.g. diatomaceous earth and then the active ingredient in the filtrate is adsorbed onto Diaion HP-20. The resin is washed with water and eluted with 50% aqueous acetone. Active fractions of eluates are concentrated under reduced pressure to remove the acetone. The concentrate is extracted with ethyl acetate, extract is concentrated to dryness under reduced pressure and the resultant residue is further purified by any optional combination of column chromatography with silica gel (developed with chloroform-methanol, 30:1), Sephadex LH-20 and the like, thereby affording a highly purified substance SF-2140.

VI. Physico-chemical properties of the substance SF-2140

(1) Color and state: Colorless crystals, neutral substance (2) Melting point: 174° to 176° C. (with decomp.)

(3) Elementary analysis: C: 59.54%, H: 5.63%, N: 7.59%

(4) Ultraviolet absorption spectrum (as shown in FIG. 1):

Maximum absorption at 222 nm ($E_1\ _{cm}^{1\%}=960$), 258 nm (sh), 265 nm ($E_1\ _{cm}^{1\%}=228$), 284 nm ($E_1\ _{cm}^{1\%}=174$), 294 nm ($E_1\ _{cm}^{1\%}=192$).

No shift with acid or alkali observed.

Figure 2:
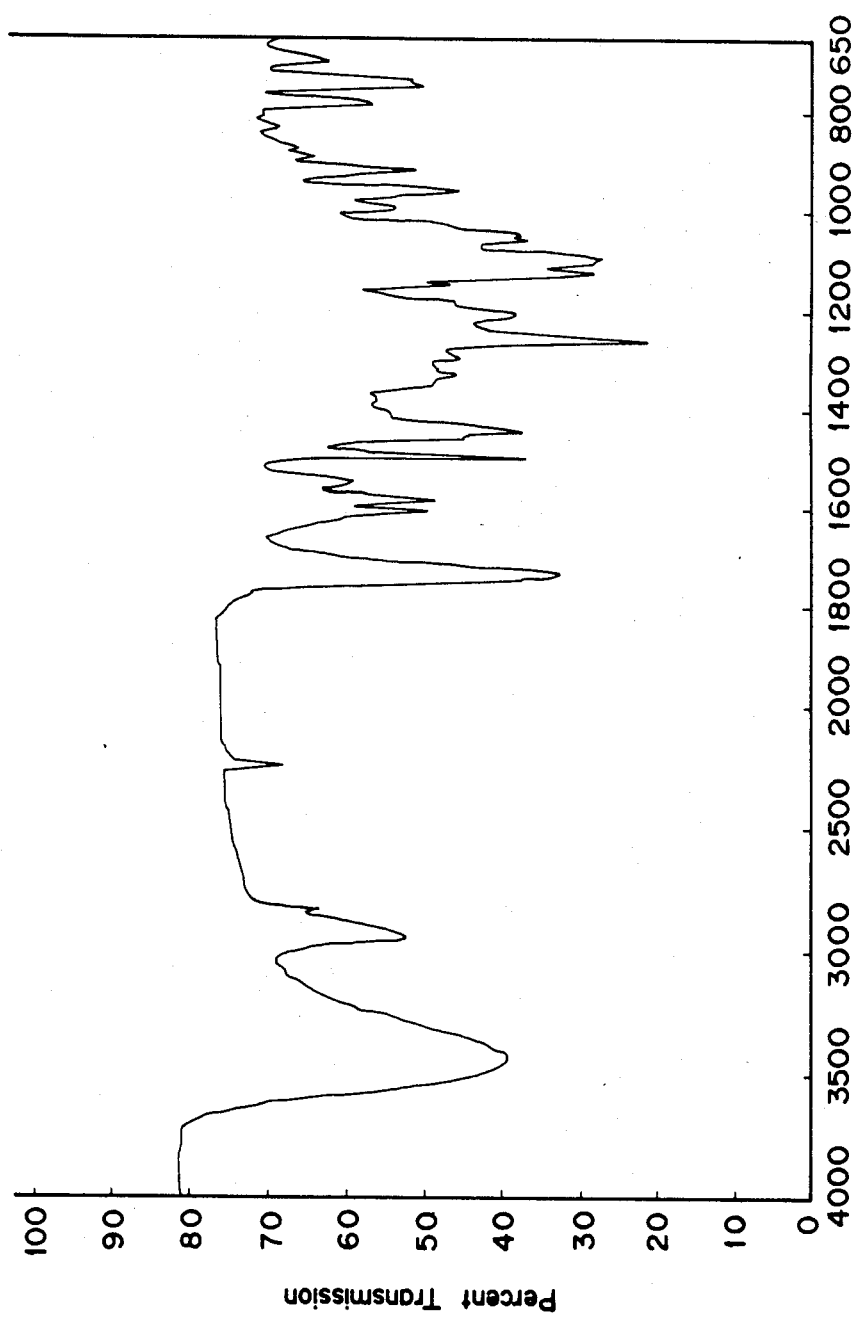
FIG. 2 shows an infrared absorption spectrum of the substance Sf-2140 in KBr tablet.

(5) Infrared absorption spectrum in KBr: As shown in FIG. 2

(6) Molecular weight (Mass spectrum): 360

(7) Molecular formula: $C_{18}H_{20}N_2O_6$ as determined upon the elementary analysis and NMR spectrum.

Figure 3:
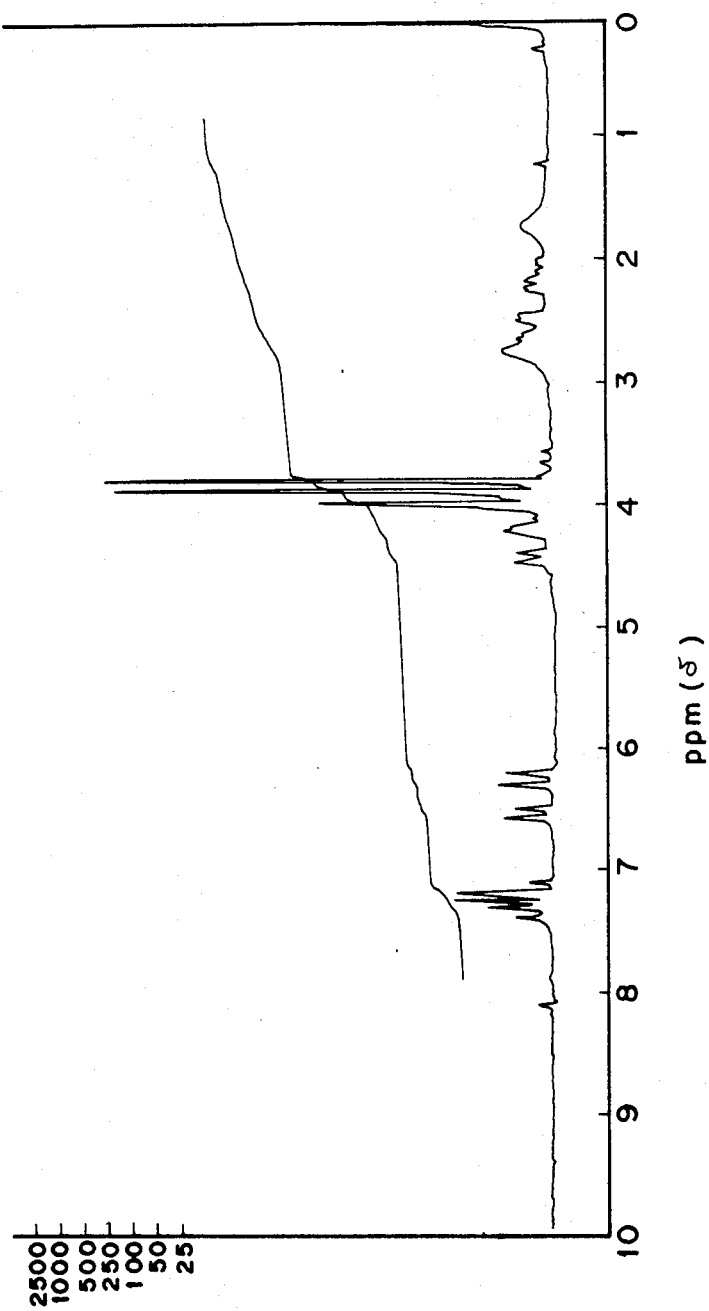
FIG. 3 shows NMR spectrum of the subtance SF-2140 measured with 100 MHz and denteriechloroform.

(8) NMR spectrum ($CDC_3$, 100 MHz, H-NMR spectrum): As shown in FIG. 3.

(9) Specific rotation: $[\alpha]_D^{20}=+50.2°$ ($C_1$ methanol)

(10) Solubility:

Easily soluble: Lower alcohol, e.g. methanol and ethanol

Soluble: Ethyl acetate, benzene, acetone, chloroform

Substantially insoluble: Hexane, water

(11) Rf value in silica gel thin layer chromatography:

Chloroform-methanol (5:1) 0.53

Ethyl acetate-benzene (2:1) 0.31

Acetone-benzene (2:1) 0.82

(12) Color reaction:

Lemiex-sulfuric acid reaction: Positive

Ninhydrin reaction: Negative

(13) Stability: Stable under acidic to neutral condition, instable under alkaline condition.

The substance SF-2140 has been regarded as a novel substance. More specifically, the known substances "Trienin" (Journal of Antibiotics, 21, 611–615, 1968) and "Mycotrienin" (Journal of Antibiotics, 20, 329–333, 1967) have a relative resemblance to the substance SF-2140 with regard to the absorption pattern in ultraviolet absorption spectrum, but they are yellow substances and quite different in elementary analysis and molecular weight from the SF-2140 substance. Thus, the substance SF-2140 can be definitely distinguished from the prior two substances. On the other hand, other known antibitotics, "Quinamycins A, B, C, D" (Journal of Antibiotics, 24, 353–359, 1971), which have respective molecular formulae, ($C_{24}H_{20}N_2O_{10}$, $C_{20}H_{16}N_2O_8$, $C_{24}H_{20}N_2O_{16}$ and $C_{22}H_{18}N_2O_9$, appear to have a relative resemblance to the SF-2140 substance having the above-defined molecular formula, but they can be definitely distinguished from the substance SF-2140 with regard to the color, ultraviolet, infrared and NMR spectra, specific rotation and others.

Also, the substance SF-2140 was found to show an antibacterial activity against various organisms as illustrated in the following Table 1.

TABLE 1

| Test organisms | Minimum Inhibitory Concentration (mcg/ml)* |
|---|---|
| *Staphylococcus aureus* 209P | 25 |
| *Staphylococcus aureus* Smith | 100 |
| *Streptococcus faecalis* ATCC 8043 | 12.5 |
| *Baciullus anthrasis* No. 119 | 6.25 |
| *Escherichia coli* No. 29 | >100 |

TABLE 1-continued

| Test organisms | Minimum Inhibitory Concentration (mcg/ml)* |
|---|---|
| Escherichia coli W3630 RGN 823 | 50 |
| Citrobacter freundii GN 346 | >100 |
| Salmonella typhi 0-901-W | 100 |
| Salmonella enteritidis No. 11 | 12.5 |
| Sarcina lutea | 50 |
| Shigella sonnei EW33 type I | >100 |
| Klebsiella pneumoniae PCI 602 | >100 |
| Proteus vulgaris OX-19 | 25 |
| Proteus morganii Kono | >100 |
| Pseudomonas aeruginosa MB 3829 | >100 |
| Pseudomonas cepacia M-0527 | 100 |

*agar dilution method

As a planar structure of the substance, the substance SF-2140 has been determined to have the following chemical structure:

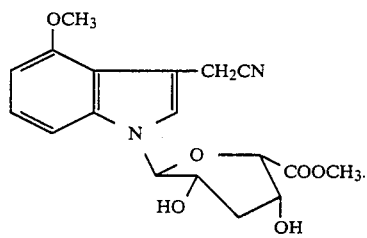

As a result of further studies on biological activities of the said substance SF-2140 made by the present inventors, it has been unexpectedly found that the substance SF-2140 can exert a potent antiviral activity and the present invention has been completed upon this finding.

It is, accordingly, a primary object of this invention to provide a new antiviral agent.

Another object is to provide a method for treatment of viral diseases in humans by administering the substance SF-2140.

These and other objects of this invention will be more apparent from the following description.

The substances Sf-2140 may be, illustratively speaking, produced, for example, as disclosed in the following Referential Example.

REFERENTIAL EXAMPLE

Cultivation of SF-2140 strain:

As the seed strain, there was employed Actinomadura sp. SF-2140 strain (FERM P-5704 which was given the international deposit number FERM BP-386 when the deposit was converted to an international deposit under the Budapest Treaty) and, as a seed culture medium, there was employed a medium of 1.0% soluble starch, 1.0% glucose, 0.5% peptone, 0.2% meat extract, 0.3% yeast extract, 0.2% fine soybean meal and 0.2% calcium carbonate. Two or three platinum loops of the seed strain were inoculated to 20 ml of the seed culture medium in a 100 ml volume Erlenmeyer flask and cultivation was effected at 28° C. for 48 hours. The resulting seed culture was in each 4 ml portion inoculated to each 80 ml of the seed culture medium in three 500 ml volume Erlenmeyer flasks and cultivation was effected at 28° C. for 4 hours.

The resulting seed culture was in each 4 ml portion inoculated to each 80 ml of a production medium in fifty 500 ml volume Erlenmeyer flasks. The production medium had composition of 1.5% glycerol, 1.0% glucose, 1.5% fine soybean meal, 0.1% yeast extract, 0.1% potassium hydrogenphosphate, 0.1% magnesium sulfate, 0.2% calcium carbonate and 0.0001% cobalt chloride (pH 7.0 before sterilization). Cultivation was effected at 28° C. for 96 hours in a shaken culture manner. After completion of the cultivation, filtration was carried out by using as a filter aid diatomaceous earth to produce 3.2 lit. of the culture broth filtrate.

Purification of Substance SF-2140:

The culture broth (3.2 lit.) obtained as above was passed through a column of 300 ml of Diaion HP-20 (trade name, manufactured by Mitsubishi Chemical Industries Ltd.) to adsorb active ingredient. The column was washed with 1 lit. of water and then eluted with 50% aqueous acetone, thereby active ingredient being eluted in the 2nd to 4th fractions, each being 200 ml fraction. The active fractions were combined, concentrated under reduced pressure to remove the acetone.

The concentrate (300 ml) was adjusted to pH 8.0 with 1N NaOH and extracted with 300 ml of ethyl acetate. The extract was concentrated under reduced pressure to dryness to give 443 mg of an oily substance (a purity of about 8%). The substance was dissolved in 3 ml of methanol, 50 ml of hexane were added to the resulting solution and the mixture was allowed to stand under ice-cooling over 1 hour to precipitate the active ingredient. After removal of the supernatant, the precipitate was dissolved in 3 ml of a mixture of chloroform and methanol (3:1), charged onto a column of 100 ml of silica gel C-200 (manufactured by Wako Junyaku Kogyo K. K.) and developed with a mixture of chloroform and methanol (30:1), thereby the active ingredient being eluted in the 14th to 19th fractions, each being 15 ml fraction. These active fractions were combined and concentrated under reduced pressure to dryness to afford 152 mg of the substance SF-2140 as a crude powder (a purity of about 35%).

The crude powder (152 mg) was dissolved in 0.5 ml of methanol, subjected to two sheets of thin layer chromatography with silica gel (manufactured by Merck & Co., Inc., F254, 20 cm cx 20 cm), developed with a developing solvent of ethyl acetate and benzene (2:1) over 3 hours and then the substance SF-2140 portions therein were scraped out and extracted twice with each 50 ml of ethyl acetate. The extract was concentrated to dryness under reduced pressure to give 38 mg of the substance SF-2140 in a high purity of about 90%.

In 2 ml of methanol were dissolved 30 mg of the substance SF-2140, the resulting solution was charged onto a column of 150 ml of Sephadex LH-20 (manufactured by Pharmacia Fine Chemicals Co.) previously packed with methanol and then developed with methanol. Active fractions were obtained as the 18th to 211st fractions in each 5 ml fraction. These active fractions were combined and concentrated to dryness under reduced pressure to give 12 mg of the substance SF-2140 as colorless crystals.

Biological tests are shown below for illustrating antiviral effects of the present antiviral agent:

Test 1

The substance SF-2140 was tested for antiviral activity against influenza virus.

(1) Test virus strains:
 (a) Influenza virus—$A_0$/PR-3
 (b) Influenza virus—$A_1$/FM-1
 (c) Influenza virus—$A_2$/Adachi
 (d) Influenza virus—B/Lee (e) Influenza virus—Horse/Miami (2) Test method:

Proliferation inhibiting activity against virus and virucidal activity were measured according to a chorioallantoic membrane culture method. Namely, chorioallantoic membrane was isolated from 15-day-old embryonated egg and a given membrance piece thereof (30 mm×30 mm) was placed into a culture test tube containing Hanks' solution, said solution containing a prescribed concentration of the substance SF-2140. Each of the above-indicated influenza virus strains was inoculated to said solution and shaken culture was conducted at 36° C. for 48 hours. Thereafter, each culture was measured for RBC of avian agglutination ability and 50% proliferation inhibiting concentration against virus was calculated therefrom. Also, virus proliferation inhibition index was determined by dividing 50% toxicity concentration of the substance SF-2140 against chorioallantoic membrane by 50% proliferation inhibiting concentration. On the other hand, each virus strain was contacted and admixed with Hanks' solution containing a prescribed concentration of the substance SF-2140 and incubation was conducted at 25° C. for 2 hours. Then, the incubated broth was diluted to a proper concentration and 50% virus proliferation inhibiting concentration and profileration inhibition index were calculated in the same manner as mentioned above to assign them as 50% virucidal concentration and virucidal index, respectively.

Further, 50% membrane-disintegration (cytotoxic) concentration was measured under the same conditions as defined above. Namely, 4 membrane pieces were incubated at an optional test compound concentration for 24 hours and dyed with 5% Trypan Blue to determine life or death of membrane cells.

(3) Test results:

The results are summarized in the following Table 2.

TABLE 2

| Treatment | Virus strain | Concentration (mcg/ml) | | |
|---|---|---|---|---|
| | | 50% Toxicity conc. | 50% Virus proliferation inhibiting conc. | 50% Virucidal conc. |
| SF-2140 | $A_0$/PR-8 | >1000 | 6.30 ($>158.7$)* | 3.2 ($>312.5$)** |
| | $A_1$/FM-1 | " | 50.5 ($>20.0$)* | 4.6 ($>217.4$)** |
| | $A_2$/Adachi | " | 100 ($>10.0$)* | 58.8 ($>17.0$)** |
| | B/Lee | " | >200 | 46.4 ($>21.6$)** |
| | Horse/Miami | " | 17.7 ($>56.5$)* | 4.6 ($>217.4$)** |

*Inhibition Index = $\frac{50\% \text{ toxic concn.}}{50\% \text{ inhibitory concn.}}$

**Virucidal Index = $\frac{50\% \text{ toxic concn.}}{50\% \text{ inhibitory concn.}}$ As apparent from the above results, the substance SF-2140 showed a proliferation inhibiting activity against the influenza virus strains, $A_0$/PR-8, $A_1$/FM-1, $A_2$Adachi and Horse/Miami.

Also, the substance SF-2140 was seen to exhibit a potent virucidal activity against all test virus in virucidal activity determination; 200 or higher against the $A_0$/PR-8, $A_1$/FM-1 and Horse/Miami strains and 15 or higher against even the $A_2$/Adachi and B/Lee strains.

Test 2

Antiviral activities of the substance SF-2140 and Amantadine (a comparative example) in mice infected with influenza virus $A_0$/PR-8 strain were tested. The substance SF-2140 and Amandatine were orally administered to mice (n=10) immediately after infection of the virus and thereafter once a day for five days with the dose as prescribed in Table 3. Results are shown together in Table 3.

TABLE 3

| Treatment | Dose | M.S.D.* | Prolong rate | Survival (%) |
|---|---|---|---|---|
| SF-2140 crystal | 125 mg/kg | $\geq 13.1$ | $\geq 103$ | 60 |
| SF-2140 crystal | 62.5 mg/kg | $\geq 13.5$ | $\geq 106$ | 70 |
| Amantadine Hcl | 250 mg/kg | $\geq 13.6$ | $\geq 107$ | 60 |
| 1% CMC | 0.15 ml/mouce | $\geq 12.7$ | 100 | 30 |

Virus: $LD_{80}$ 1 kg/cm²/10 min. (Inhalation)
M.S.D: mean survival days

Test 3

Antiviral activities of the substance SF-2140 and Amantadine in mice infected with influenza virus $A_0$/PR-8 strain were tested. The substance SF-2140 and Amantadine were intraperitoneally administered immediately after infection of the virus and thereafter once a day for five days with the dose as prescribed in Table 4. Results are shown together in Table 4.

TABLE 4

| Treatment | Dose (mg/kg) | Grade of Lesion | | Inhibition percent of consolidation (%) |
|---|---|---|---|---|
| | | ΣL/M | % | |
| SF-2140 crystal | 100 | 14.5/40 | 36.3 | 56.7 |
| SF-2140 crystal | 50 | 14.5/40 | 36.3 | 56.7 |
| SF-2140 crystal | 25 | 17.0/40 | 42.5 | 49.2 |
| Amantadine HCl | 100 | 15.5/40 | 38.8 | 53.8 |
| Amantadine HCl | 50 | 19.5/40 | 48.8 | 41.8 |
| Virus control | — | 33.5/40 | 83.8 | — |

Test 4

Serum level of the substance SF-2140 after intraperitoneal administration in mice (n=5) was observed to obtain the results shown in Table 5.

TABLE 5

| Time after administration (min) | Concentration (mcg/ml): Biological assay |
|---|---|
| 5 | 30 |
| 10 | 42 |
| 20 | 55 |
| 30 | 45 |
| 60 | 27 |
| 90 | 0 |

Dose: 200 mg/kg (1% CMC)

Test 5

Serum level of the substance SF-2140 after oral administration in mice (n=3) was observed to obtain the results shown in Table 6.

TABLE 6

| Time after administration (min) | Concentration (mcg/ml): HPLC |
| --- | --- |
| 30 | 15 |
| 60 | 7 |
| 180 | 0 |

Dose: 125 mg/kg (5% arabin gum)

Acute toxicity

Acute toxicity ($LD_{50}$ value) of the substance SF-2140, the active ingredient in the present antiviral agent, was not less than 500 mg/kg in mice via intraperitoneal administration. This $LD_{50}$ value demonstrates that the substance SF-2140 can be safely applied as an antiviral agent to human beings and other animals.

Administration and dose:

The present antiviral agent may be formulated in various pharmaceutical composition forms according to conventional preparation techniques. The pharmaceutical composition may be of any preparation forms for oral and parenteral administration including aerosol treatment; typically, inhalant, capsules, tablets, syrups, emulsions, aqueous suspensions, solutions or suspension for injection and so on, but it is preferable to orally administer the present agent formulated in an inhalant.

The usual dosage of this antiviral agent may be varied depending upon the severity of diseases, the weight and age of the patients being treated and other factors, but the active substance may be usually administered in the range of 0.05 to 25 g per day and in two to four divided doses per day.

Formulation Example 5 g of the substance SF-2140 was dissolved into dioxane and 15 g of PVP (polyvinylpyrrolidone, molecular weight: about 10,000) into water. These were respectively freeze-dried to obtain powdery products, which were mixed together to obtain a mixed powdery product. The powdery product was then diluted with water to have a concentration of 0.3%, thereby preparing an inhalant for a aerosol treatment.

We claim:

1. A method for treatment of viral diseases which comprises administering a pharmaceutically effective amount of a substance SF-2140 represented by the following formula:

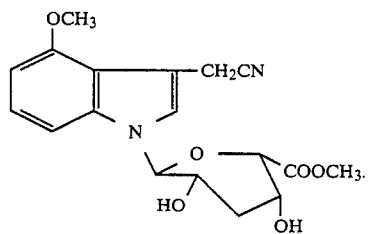

2. The method according to claim 1, wherein the substance SF-2140 is administered in the range of 0.05 to 25 g per day and in two to four divided doses per day.

* * * * *

UNITED STATES PATENT AND TRADEMARK OFFICE
CERTIFICATE OF CORRECTION

PATENT NO. : 4,536,398

DATED : August 20, 1985

INVENTOR(S) : Tatsuo ITO et al

It is certified that error appears in the above-identified patent and that said Letters Patent is hereby corrected as shown below:

Column 5, replace the equation appearing between lines 18 - 28 with the following:

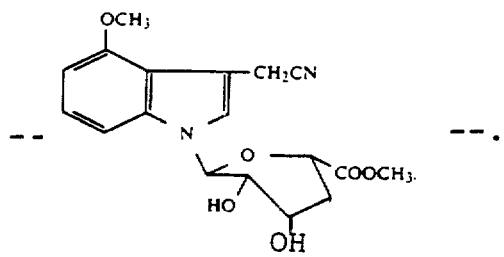

UNITED STATES PATENT AND TRADEMARK OFFICE
CERTIFICATE OF CORRECTION

PATENT NO. : 4,536,398

DATED : August 20, 1985

INVENTOR(S) : Tatsuo ITO et al

It is certified that error appears in the above-identified patent and that said Letters Patent is hereby corrected as shown below:

Column 10 (claim 1), replace the equation appearing between lines 18 - 30 with the following:

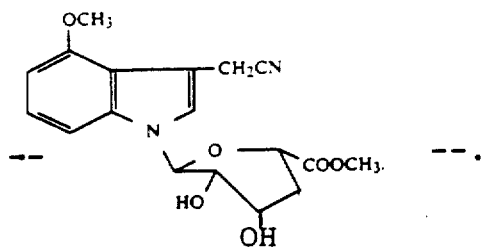

Signed and Sealed this

Twenty-eighth Day of January 1986

[SEAL]

Attest:

DONALD J. QUIGG

Attesting Officer     Commissioner of Patents and Trademarks